(12) United States Patent
Pavliv et al.

(10) Patent No.: US 8,871,810 B2
(45) Date of Patent: *Oct. 28, 2014

(54) TREATING CRITICALLY ILL PATIENTS WITH INTRAVENOUS IBUPROFEN

(75) Inventors: Leo Pavliv, Cary, NC (US); Amy Dix Rock, Nashville, TN (US)

(73) Assignee: Cumberland Pharmaceuticals Inc., Nashville, TN (US)

( * ) Notice: Subject to any disclaimer, the term of this patent is extended or adjusted under 35 U.S.C. 154(b) by 331 days.

This patent is subject to a terminal disclaimer.

(21) Appl. No.: 12/646,499

(22) Filed: Dec. 23, 2009

(65) Prior Publication Data

US 2011/0028553 A1 Feb. 3, 2011

Related U.S. Application Data

(63) Continuation-in-part of application No. 12/570,912, filed on Sep. 30, 2009, now abandoned.

(60) Provisional application No. 61/230,324, filed on Jul. 31, 2009, provisional application No. 61/230,342, filed on Jul. 31, 2009, provisional application No. 61/225,778, filed on Jul. 15, 2009.

(51) Int. Cl.
| | |
|---|---|
| *A01N 37/10* | (2006.01) |
| *A61K 31/19* | (2006.01) |
| *A61K 31/197* | (2006.01) |
| *A61K 31/192* | (2006.01) |

(52) U.S. Cl.
CPC .............. *A61K 31/192* (2013.01); *A61K 31/197* (2013.01)
USPC .......................................... 514/570; 514/565

(58) Field of Classification Search
None
See application file for complete search history.

(56) References Cited

U.S. PATENT DOCUMENTS

| | | | |
|---|---|---|---|
| 4,279,926 A | 7/1981 | Bruzzese | |
| 4,309,421 A | 1/1982 | Ghyczy | |
| 4,859,704 A | 8/1989 | Haas | |
| 4,861,797 A | 8/1989 | Haas | |
| 5,200,558 A | 4/1993 | Kkwan | |
| 5,463,117 A | 10/1995 | Stroppolo | |
| 6,005,005 A | 12/1999 | Stroppolo | |
| 6,342,530 B1 | 1/2002 | Darko | 514/561 |
| 6,423,746 B1 | 7/2002 | Yarbrough | 514/561 |
| 6,727,286 B2 | 4/2004 | Pavliv | 514/565 |
| 2004/0132823 A1 | 7/2004 | Pavliv | 514/565 |
| 2004/0253244 A1 | 12/2004 | Shelton et al. | |
| 2008/0058302 A1 | 3/2008 | Dolle et al. | |
| 2009/0048345 A1 | 2/2009 | Lee | 514/570 |
| 2009/0054413 A1 | 2/2009 | Henriksson et al. | |
| 2010/0015237 A1 | 1/2010 | Moses et al. | |

OTHER PUBLICATIONS

Omoigui, Med Hypotheses, 2007; 69(6): 1169-1178.*
Office Action dated Mar. 9, 2011 issued in connection with corresponding U.S. Appl. No. 12/830,991.
Applicant's Response to Office Action dated Feb. 4, 2011 filed in connection with corresponding U.S. Appl. No. 12/830,991.
Office Action dated Nov. 10, 2010 issued in connection with corresponding U.S. Appl. No. 12/830,991.
Applicant's Response to Office Action dated Oct. 27, 2010 filed in connection with corresponding U.S. Appl. No. 12/830,991.
Office action dated Sep. 28, 2010 issued in connection with corresponding U.S. Appl. No. 12/830,991.
Applicant's Response to Office Action dated Sep. 27, 2010 filed in connection with corresponding U.S. Appl. No. 12/830,991.
Applicant's Response to Office Action dated Sep. 8, 2010 filed in connection with corresponding U.S. Appl. No. 12/830,991.
Office Action dated Aug. 9, 2010 issued in connection with corresponding U.S. Appl. No. 12/830,991.
Office Action dated Mar. 18, 2011 issued in connection with corresponding U.S. Appl. No. 12/570,912.
Stanik-Hutt "Pain management in the critically ill", Critical Care Nurse, vol. 23, No. 2, Apr. 2003, pp. 99-103.
Hogarth et al "Management of sedation in mechanically ventilated patients", Curr. Opin. Crit. Care vol. 10, 2004, pp. 40-46.
International Search Report, dated Apr. 23, 2010, in connection with corresponding International Application No. PCT/US10/27096.
Office Action dated Sep. 8, 2011, in connection with corresponding U.S. Appl. No. 12/830,991.
Office Action dated Oct. 7, 2011 issued in connection with corresponding U.S. Appl. No. 12/722,682.
Office Action dated Oct. 28, 2011 issued in connection with corresponding U.S. Appl. No. 12/830,991.
Applicant's Response to Office Action dated Sep. 8, 2011 filed in connection with corresponding U.S. Appl. No. 12/830,991.
Office Action dated Jul. 13, 2011 issued in connection with corresponding U.S. Appl. No. 12/830,991.
Office Action dated May 11, 2011 issued in connection with corresponding U.S. Appl. No. 12/830,991.
Applicant's Response to Office Action dated May 11, 2011 filed in connection with corresponding U.S. Appl. No. 12/830,991.
*Ibuprofen*: Drug Information Provided by Lexi-Comp., Ibuprofen: Drug Information Provided by Lexi-Comp: Merck Manual Professional, http://www.merck.com/mmpe/print/lexicomp/ibuprofen.html, pp. 1-21, 2010 JC.
*Pharmacokinetic Data*, Cadolor® (ibuprofen) injection, Medical information: PK, Sep. 1, 2009, Cumberland Pharmaceuticals, pp. 1-8.
Boucher, Bradley A., et al., *Pharmacokinetic Changes in Critical Illness*, Grit Care Clin 22 (2006), pp. 225-271.
Davies, Neal M., *Clinical Pharmacokinetics of Ibuprofen: The First 30 Years*, Clin Pharmacokinet Feb. 1998: 34(2) pp. 101-154.

(Continued)

*Primary Examiner* — Wu-Cheng Winston Shen
*Assistant Examiner* — Jean Cornet
(74) *Attorney, Agent, or Firm* — Davidson, Davidson & Kappel, LLC

(57) ABSTRACT

Methods of treating at least one condition chosen from pain, inflammation, and fever in a critically ill patient in need thereof, comprising administering to the critically ill patient an intravenous pharmaceutical composition comprising ibuprofen using a first dosage regimen, wherein the first dosage regimen produces a first pharmacokinetic profile in critically ill patients that is about equivalent to a second pharmacokinetic profile produced by administration of the intravenous pharmaceutical composition using a second dosage regimen of ibuprofen to non-critically ill patients, wherein the at least one condition of the critically ill patient is thereby treated.

13 Claims, 5 Drawing Sheets

(56) References Cited

OTHER PUBLICATIONS

Morris, Peter E., et al., *A multi-center, randomized, double-blind, parallel, placebo-controlled trial to evaluate the efficacy, safety, and pharmacokinetics of intravenous ibuprofen for the treatment of fever in critically ill and non-critically ill adults*, Critical Care, 2010, 14:R125, pp. 1-13.

Gordan R. Bernard, et al., *The Effect of Ibuprofen on the Physiology and Survival of Patients With Sepsis*, The New England Journal of Medicine, vol. 336, No. 13, p. 912-918 (1997).

Product Information: Caldolorim™, Jun. 2009.

SCCM: *IV Ibuprofen Controls Fever in Critically Ill Patients*, Feb. 3, 2009.

JV Aranda, et al., *Pharmacokinetics and protein binding of intravenous ibuprofen in the premature newborn infant*, Acta Paediatr 86: 289-93, 1997.

Morris, Peter, et al., *A multi-center, randomized, double-blind, placebo-controlled trial of the efficacy and safety of intravenous ibuprofen in febrile adults*, Crit Care Med 2008, vol. 36, No. 12 (Suppl), p. A18, Abstract.

Grossman, et al., Pathophysiology of Cystic Fibrosis: Implication for critical care Nurses, Crit. Care Nurse, 2005, vol. 25, pp. 46-51.

Konstan, et al., Ibuprofen in children with cystic fibrosis; pharmacokinetics and adverse effects, J. Pediatr. Jun. 1991, vol. 116, No. 6, pp. 956-964, Abstract.

International Search Report and Written Opinion mailed on Jul. 13, 2010 issued in connection with corresponding PCT Patent Application No. PCT/US10/36015.

U.S. Appl. No. 12/699,595, Pavliv.

U.S. Appl. No. 12/722,682, Pavliv.

Guindon et al., "Antihyperalgesic effects of local injections of anandamide, ibuprofen, rofecoxib and their combinations in a model of neuropathic pain", Neuropharmacology, Jun. 2006;50(7):814-823.

Murry, et al., "Pharmacokinetics of Ibuprofen in Patients with Cystic Fibrosis", Pharmacotherapy 1999, JC;19(3):340-345.

Hirakawa, Yoshihisa, et al. "Association of renal insufficiency with in-hospital mortality among Japanese patients with acute myocardial infarction undergoing percutaneous coronary interventions." International heart journal vol. 47 (2006); pp. 745-752.

Notice of Opposition concerning the corresponding Indian Patent Application 5360/CHENP/2012.

\* cited by examiner

TREATING CRITICALLY ILL PATIENTS WITH INTRAVENOUS IBUPROFEN

This claims the benefit under 35 U.S.C. §119(e) of U.S. Provisional Patent Application No. 61/230,324, filed Jul. 31, 2009, the entire disclosure of which is hereby incorporated herein by reference for all purposes. This application also claims benefit of priority under 35 U.S.C. §120 to U.S. patent application Ser. No. 12/570,912, filed Sep. 30, 2009, the entire disclosure of which is hereby incorporated herein by reference for all purposes. This application also claims benefit under 35 U.S.C. §119(e) of U.S. Provisional Patent Application No. 61/230,342, filed Jul. 31, 2009, and U.S. Provisional Patent Application No. 61/225,778, filed Jul. 15, 2009.

Provided are methods for treating critically ill patients by intravenously administering a pharmaceutical composition comprising an effective amount of 2-(4-isobutylphenyl) propionic acid.

2-(4-isobutylphenyl) propionic acid, whose International Nonproprietary Name is ibuprofen, is a well-known anti-inflammatory drug having a molecular weight of 206.28 and the following chemical structure:

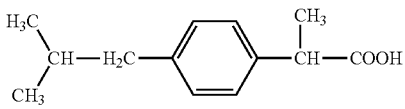

(Merck Index 12th ed., n4925, page 839). Originally patented in the 1960's, ibuprofen is now marketed generically, as well as under the tradenames of Motrin®, Advil®, and Nuprin® for the treatment of pain, inflammation, and fever. The U.S. Food and Drug Administration recently approved a new formulation of ibuprofen for intravenous administration to be marketed under the trade name Caldolor®.

Ibuprofen is readily available as the racemic mixture ((RS)-Ibuprofen) of the two enantiomers, (R)-Ibuprofen and (S)-Ibuprofen. Even though the (S) enantiomer is the biologically active form, most preparations contain the racemic mixture since the (R) enantiomer is converted to the active (S) form in-vivo. For simplicity, hereinafter the term "ibuprofen" will be used to indicate any one of the (R) enantiomer, the (S) enantiomer, or the racemate.

Although ibuprofen has many advantages over other analgesics such as aspirin and acetaminophen, it is very poorly soluble in water. Thus, certain dosage forms of ibuprofen, especially injectable liquids, have been difficult to develop. Several U.S. patents have addressed this problem.

For example, U.S. Pat. No. 4,309,421 appears to describe water-soluble complexes of ibuprofen and phospholipids suitable for parenteral administration. U.S. Pat. Nos. 4,859,704 and 4,861,797 appear to describe the synthesis of alkali metal salts of ibuprofen for preparing a liquid ibuprofen formulation.

Other U.S. patents appear to address this problem by preparing an ibuprofen salt with a basic amino acid as the active pharmaceutical ingredient and then solubilizing the salt to produce a liquid dosage form.

For example, U.S. Pat. No. 5,200,558 appears to describe enhanced analgesic effects of S (+) ibuprofen as salts of L and D amino acids, including arginine, in various dosage forms, including as an injectable solution. U.S. Pat. No. 4,279,926 appears to describe the use of basic amino acid salts of propionic acids for relieving pain and treating inflammatory conditions. Similarly, U.S. Pat. No. 5,463,117 appears to describe the preparation of salts of ibuprofen with basic amino acids. Finally, U.S. Pat. No. 6,005,005 appears to describe a liquid composition for oral use containing ibuprofen and arginine.

U.S. Pat. No. 6,727,286 B2 describes, among other things, a pharmaceutical composition comprising an aqueous solution of arginine and ibuprofen, wherein the molar ratio of arginine to ibuprofen is less than 1:1, as well as a method of making the same. That patent also provides a method of treating a condition chosen from pain, inflammation, fever, and/or other conditions alleviated by ibuprofen comprising administering a pharmaceutical composition comprising an aqueous solution of arginine and ibuprofen, wherein the molar ratio of arginine to ibuprofen is less than 1:1. The entire contents of U.S. Pat. No. 6,727,286 B2 are hereby incorporated herein by reference.

The U.S. Food and Drug Administration recently approved a new formulation of ibuprofen for intravenous administration to be marketed under the trade name Caldolor® by Cumberland Pharmaceuticals, Inc. Caldolor® contains the active ingredient ibuprofen. As described on the labeling for Caldolor®, "each 1 mL of solution contains 100 mg of ibuprofen in Water for Injection, USP. The product also contains 78 mg/mL arginine at a molar ratio of 0.92:1 arginine:ibuprofen. The solution pH is about 7.4." Caldolor® is sterile and is intended for intravenous administration only.

Caldolor® possesses antiinflammatory, analgesic, and antipyretic activity. As such, Caldolor® is indicated in adults for the management of mild to moderate pain and the management of moderate to severe pain as an adjunct to opioid analgesics. 400 mg to 800 mg of Caldolor® is administered intravenously every 6 hours as necessary to treat pain. Caldolor® is also indicated for the reduction of fever in adults. 400 mg of Caldolor® is administered intravenously, followed by 400 mg every 4 to 6 hours or 100-200 mg every 4 hours as necessary to treat fever.

SUMMARY OF THE INVENTION

Provided are methods of treating at least one condition chosen from pain, inflammation, and fever in a critically ill patient in need thereof. The methods include administering to the critically ill patient an intravenous pharmaceutical composition comprising ibuprofen using a first dosage regimen, wherein the first dosage regimen produces a first pharmacokinetic profile in critically ill patients that is about equivalent to a second pharmacokinetic profile produced by administration of the intravenous pharmaceutical composition using a second dosage regimen of ibuprofen to non-critically ill patients, wherein the at least one condition of the critically ill patient is thereby treated.

In some embodiments the first dosage regimen includes administration of at least one dose of ibuprofen that is higher than any dose of ibuprofen administered in the second dosage regimen. In some embodiments the first dosage regimen comprises a dosing interval that is shorter than any dosing interval used in the second dosage regimen. In some embodiments the first pharmacokinetic profile produced by administration of the first dosage regimen of ibuprofen to critically ill patients includes an area under plasma concentration-time curve (AUC) over a period of time that is about equivalent to the AUC over the period of time of the second pharmacokinetic profile produced by administration of the second dosage regimen of ibuprofen to non-critically ill patients.

In some embodiments the first dosage regimen includes administration of a dose of ibuprofen of greater than a dose administered to non-critically ill patients in a second dosage regimen, wherein the dose administered in the first dosage regiment is from 100 to 1600 mg. In some embodiments the dose administered in the first dosage regimen is selected from 100 mg, 150 mg, 200 mg, 250 mg, 300 mg, 350 mg, 400 mg, 450 mg, 500 mg, 550 mg, 600 mg, 650 mg, 700 mg, 800 mg, 1000 mg, 1200 mg, 1400 mg, 1600 mg, 2400 mg, and 3200 mg. In some embodiments the dose administered in the first dosage regimen is selected from 100 mg, 200 mg, 400 mg, and 800 mg.

In some embodiments the first dosage regimen includes a dosing interval that is shorter than any dosing interval used in the second dosage regimen. In some embodiments the at least one condition is pain. In some embodiments the at least one condition is inflammation. In some embodiments the at least one condition is fever.

In some embodiments the critically ill patient is a patient receiving at least one form of treatment selected from treatment with a vasopressor and mechanical ventilation.

In some embodiments the pharmaceutical composition is an aqueous solution of arginine and ibuprofen.

In some embodiments the molar ratio of arginine to ibuprofen is selected from less than or equal to 1:1, less than or equal to 0.99:1, less than or equal to 0.98:1, less than or equal to 0.97:1, less than or equal to 0.96:1, less than or equal to 0.95:1, less than or equal to 0.94:1, less than or equal to 0.93:1, less than or equal to 0.92:1, less than or equal to 0.91:1, less than or equal to 0.90:1, less than or equal to 0.60:1. In some embodiments the pharmaceutical composition is Caldolor®.

In some embodiments administering the first dosage regimen to critically ill patients reduces the at least one condition chosen from pain, inflammation, and fever to an about equivalent extent to the reduction of the at least one condition chosen from pain, inflammation, and fever achieved in non-critically ill patients to which the second dosage regimen is administered.

The invention is further directed to a method of treating at least one condition chosen from pain, inflammation, and fever in critically ill patients in need thereof, comprising administering to the critically ill patient an intravenous ibuprofen pharmaceutical composition in a dose from about 400 mg to about 800 mg every 4 to 6 hours, to attain a mean Cmax of about 20.8 µg/ml to about 75 µg/ml.

In certain preferred embodiments, the method further comprises administering to the critically ill patient an intravenous ibuprofen pharmaceutical composition in a dose from about 400 mg to about 800 mg every 4 to 6 hours, to attain a mean AUC of about 36.8 µg·h/ml to about 117.5 µg·h/ml.

The invention is further directed to a method of treating at least one condition chosen from pain, inflammation, and fever in critically ill patients in need thereof, comprising administering to the critically ill patients an intravenous ibuprofen pharmaceutical composition in an amount sufficient to attain a desired Cmax and AUC for those patients, wherein the dose of intravenous ibuprofen administered to the critically ill patients is about twice the dose of intravenous ibuprofen that provides a substantially equivalent Cmax and AUC when administered to non-critically ill patient population, such that the dose reduces at least one condition chosen from pain, inflammation, and fever in the critically ill patient.

As used herein the term "treat," "treating" or "treatment" refers to the administration of ibuprofen to an individual who already manifests, has in the past manifested, and/or is at risk of manifesting at least one symptom of a disease or condition, that can be reduced or alleviated by administration of ibuprofen. Examples of such diseases and conditions include pain, inflammation, and fever.

Figure 1:
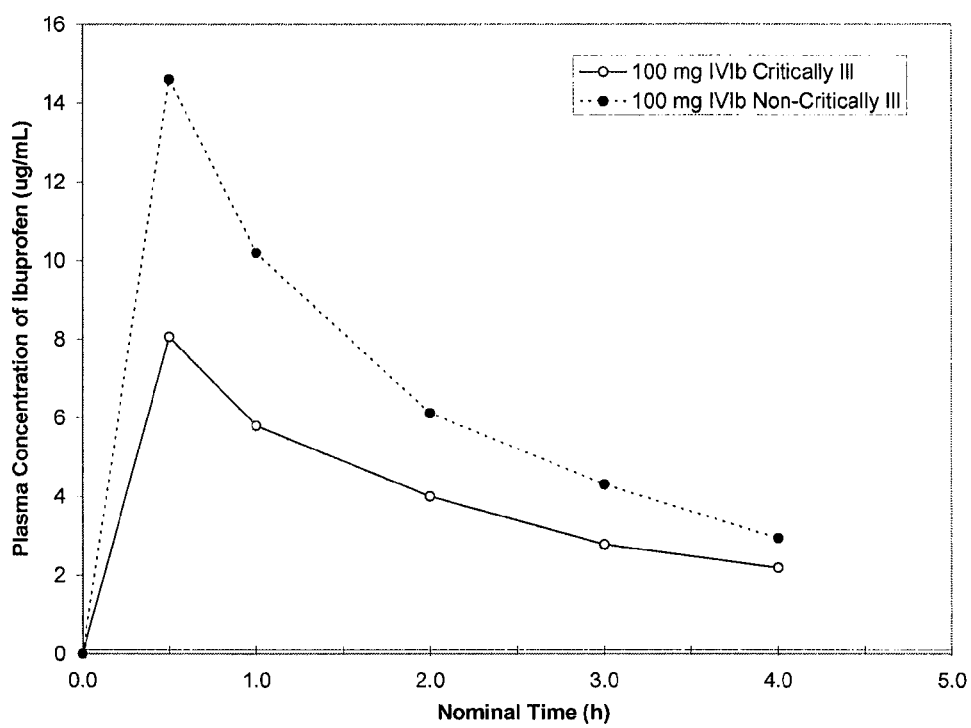
FIG. 1 shows mean ibuprofen plasma concentrations (hours 0-4) following administration of 100 mg IVIb in critically ill versus non-critically ill patients.

Provided herein are methods of treating at least one condition chosen from pain, inflammation, and fever in a critically ill patient in need thereof.

DETAILED DESCRIPTION OF THE INVENTION

In some embodiments a "critically ill" patient is a patient receiving at least one of vasopressor support and mechanical ventilation. In another embodiment of the invention a "critically ill" patient is at least one of a patient receiving vasopressor support, receiving mechanical ventilation, being treated in an Intensive Care Unit ("ICU"), e.g., of a hospital, being administered large volumes of blood products, especially packed red cells, undergoing dialysis, especially continuous veno-venous hemofiltration, receiving multiple antibiotics, having a pulmonary artery catheter and having an arterial blood pressure catheter inserted. These criteria for critically ill patients are exemplary only, and one skilled in the art will understand that other indicia of a patient in a critically ill state are possible and are considered to be encompassed by the term "critically ill" as it is used herein. As used herein a patient receiving "vasopressor support" refers to a patient unable to maintain a sufficient blood pressure who is consequently being treated with a vasopressor to raise the patient's bloodpressure. Examples of vasopressor support medications include Norepinephrine (marketed for example under the brand name Levophed®).

Certain methods described herein comprise administering to the critically ill patient an intravenous pharmaceutical composition comprising ibuprofen. Intravenous pharmaceutical compositions of ibuprofen include any formulation suitable for administration to a patient via any intravenous method, including a bolus. In some embodiments the rate of infusion is such that the dose is administered over a period of about 30 minutes. In some embodiments the rate of infusion is such that the dose is administered over a period of less than 30 minutes. In some embodiments the rate of infusion is such that the dose is administered over a period of greater than 30 minutes.

In alternative embodiments of the treatment methods described herein a pharmaceutical formulation comprising ibuprofen is administered to a patient via an injection method. In such embodiments the pharmaceutical formulation of ibuprofen is a formulation suitable for administration to a patient via the injection method. Suitable injection methods include, in addition to intravenous injection, intraarterial infusion, intramuscular injection, transdermal injection, and subcutaneous injection.

Suitable carriers for intravenous administration include physiological saline or phosphate buffered saline (PBS), and solutions containing solubilizing agents, such as glucose, polyethylene glycol, and polypropylene glycol and mixtures thereof.

The formulation may include an aqueous vehicle. Aqueous vehicles include, by way of example and without limitation, Sodium Chloride Injection, Ringers Injection, Isotonic Dextrose Injection, Sterile Water Injection, Dextrose, and Lactated Ringers Injection. Nonaqueous parenteral vehicles include, by way of example and without limitation, fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include, by way of example and without limitation, sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include, by way of example and without limitation, ethyl alcohol, polyethylene glycol and propylene glycol for water miscible vehicles and sodium hydroxide, hydrochloric acid, citric acid or lactic acid for pH adjustment.

Typically a therapeutically effective dosage is formulated to contain a concentration of at least about 0.1% w/w up to about 90% w/w or more, such as more than 1% w/w of ibuprofen.

As used herein a "dosage regimen" refers to the protocol used to administer an intravenous pharmaceutical formulation comprising ibuprofen to a patient. In some embodiments the dosage regimen comprises a dose amount and dosing interval. In some embodiments the dosage regimen further comprises a dosing duration. As used herein "dosing duration" refers to the period of time over which a dose is administered. For example, if a volume of pharmaceutical composition comprising 400 mg of ibuprofen is administered over a dosing duration of 30 min and administration of a dose is initiated every 6 hours, then the dosage regimen is 400 mg, every six hours, administered over 30 minutes. In some embodiments the dosage duration is defined simply as 400 mg, every six hours.

In some embodiments described herein a dosage regimen for critically ill patients is defined as one that produces a first pharmacokinetic profile in critically ill patients that is about equivalent to a second pharmacokinetic profile produced by administration of a second dosage regimen of ibuprofen to non-critically ill patients. As used herein, two pharmacokinetic profiles are "about equivalent" if they are defined by at least one parameter that is about equivalent between the two profiles. Non-limiting examples of such parameters include the area under plasma concentration over time curve (AUC) and the maximal plasma concentration reached following administration of a dose (Cmax).

In some embodiments two pharmacokinetic parameters are about equivalent if the lower value is greater than 70%, greater than 75%, greater than 80%, greater than 85%, greater than 90%, greater than 95%, greater than 96%, greater than 97%, greater than 98%, or greater than 99% of the higher value.

The pharmacokinetic profiles of two dosage regimens are compared by determining the average pharmacokinetic profile in a population of patients receiving the first dosage regimen, determining the average pharmacokinetic profile in a population of patients receiving the second dosage regimen, and then comparing those two population dosage regimens.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The present invention contemplates the use of intravenous formulations of ibuprofen that are bioequivalent to the Caldolor® formulations and administrations disclosed herein, as defined by typical FDA criteria. In particular, it is contemplated that formulations and methods exhibiting at least one of the Cmax and AUC profiles within 80-125% of the Cmax and AUC values contemplated herein for the administration of intravenous ibuprofen (Caldolor®).

Thus, in certain embodiments, the invention is directed to a method of treating at least one condition chosen from pain, inflammation, and fever in critically ill patients in need thereof receiving, e.g., at least one of pressor support and mechanical ventilation, comprising administering to the critically ill patient an intravenous ibuprofen pharmaceutical composition in a dose from about 400 mg to about 800 mg every 4 to 6 hours, to attain a mean Cmax of about 20.8 µg/ml to about 75 µg/ml. The value of mean Cmax of 20.8 µg/ml is obtained by calculating 80% of the approximately 26 (25.7) µg/ml Cmax value obtained in Example 1. The value of mean Cmax of about 75 µg/ml is obtained by taking 50% of the approximately 120 µg/ml Cmax value surmised from Examples 2-3 (60 µg/ml), and calculating 125% of that number. (See paragraph 075).

In certain preferred embodiments, the method further comprising administering to the critically ill patient an intravenous ibuprofen pharmaceutical composition in a dose from about 400 mg to about 800 mg every 4 to 6 hours, to attain a mean AUC of about 36.8 µg·h/ml to about 117.5 µg·h/ml. The value of mean AUC of 36.8 µg·h/ml is obtained by calculating 80% of the approximately 46 (45.937) µg·h/ml AUC value obtained in Example 1. The value of mean AUC of 117.5 µg·h/ml is obtained by taking 50% of the approximately 188 µg·h/ml AUC value surmised from Examples 2-3 (94 µg·h/ml), and calculating 125% of that number. (See paragraph 075).

The invention is further directed to a method of treating at least one condition chosen from pain, inflammation, and fever in critically ill patients in need thereof receiving at least one of pressor support and mechanical ventilation, comprising administering to the critically ill patients an intravenous ibuprofen pharmaceutical composition in an amount sufficient to attain a desired Cmax and AUC for those patients, wherein the dose of intravenous ibuprofen administered to the critically ill patients is about twice the dose of intravenous ibuprofen that provides a substantially equivalent Cmax and AUC when administered to a non-critically ill patient population, such that the dose reduces at least one condition chosen from pain, inflammation, and fever in the critically ill patient. In certain preferred embodiments of this method, the dose of intravenous ibuprofen administered to the critically ill patients is 200 mg and provides a mean Cmax within about 80% to about 125% of 11.5 µg/ml. In certain additional preferred embodiments of this method, the dose of intravenous ibuprofen administered to the critically ill patient is 200 mg and provides a mean $(AUC)0\text{-}4$ within about 80% to about 125% of 19.6 µg.h/ml. In certain preferred embodiments of this method, the dose of intravenous ibuprofen administered to the critically ill patients is 400 mg and provides a mean Cmax within about 80% to about 125% of 25.7 µg/ml. In certain additional preferred embodiments of this method, the dose of intravenous ibuprofen administered to the critically ill patient is 400 mg and provides a mean $(AUC)0\text{-}4$ within about 80% to about 125% of 45.9 µg.h/ml. In other embodiments of this method, the dose of intravenous ibuprofen administered to the critically ill patients is 800 mg and provides a mean Cmax within about 80% to about 125% of 60 µg/ml. In certain additional preferred embodiments of this method, the dose of intravenous ibuprofen administered to the critically ill patients is 800 mg and provides a mean $(AUC)0\text{-}t$ within about 80% to about 125% of 94 µg.h/ml.

The invention is further directed to a method of treating at least one condition chosen from pain, inflammation, and fever in critically ill patients in need thereof receiving at least one of pressor support and mechanical ventilation, comprising administering to the critically ill patient an intravenous pharmaceutical composition comprising ibuprofen at a dosage of (i) 100 mg ibuprofen to attain a mean Cmax of about 8.2 µg/ml±6.3; or (ii) 200 mg ibuprofen to attain a mean Cmax of about 11.5 µg/ml±2.8; or (iii) 400 mg ibuprofen to attain a mean Cmax of about 25.7 µg/ml±8.3 or (iv) 800 mg ibuprofen to attain a mean Cmax within 80-125% of about 60 µg/ml. In certain preferred embodiments of this method, the dose of ibuprofen produces a mean area under plasma concentration-time curve $(AUC)0\text{-}4$ of about 16.1 µg·h/ml±14.6 for a dose of 100 mg ibuprofen; a mean area under plasma concentration-time curve $(AUC)0\text{-}4$ of about 19.6 µg·h/ml±7.0 for a dose of 200 mg ibuprofen; a mean area under plasma concentration-time curve $(AUC)0\text{-}4$ of about 45.9 µg·h/ml±16.2 for a dose of 400 mg ibuprofen; or a mean area under plasma concentration-time curve $(AUC)0\text{-}t$ within 80-125% of about 94 µg·h/ml for a dose of 800 mg ibuprofen.

Further embodiments of the invention are directed to a method of treating at least one condition chosen from pain, inflammation, and fever in critically ill patients in need thereof receiving at least one of pressor support and mechanical ventilation, comprising administering to the critically ill patients an intravenous ibuprofen pharmaceutical composition in an amount sufficient to attain a desired Cmax and AUC for those patients, wherein the dose of intravenous ibuprofen administered to the critically ill patients provides a Cmax and AUC which is from about 50% to about 61.2% of the Cmax and AUC for that dose of intravenous ibuprofen when administered to a non-critically ill patient population, such that the dose reduces at least one condition chosen from pain, inflammation, and fever in the critically ill patient.

The following example represents specific embodiments of the foregoing discovery, and is not representative of the entire scope of the invention.

Example 1

This study was conducted in hospitalized patients who were stratified by severity of illness (critically ill vs. non-critically ill). Critically ill patients were defined as receiving vasopressor support and/or mechanical ventilation. Patients received intravenous ibuprofen (Caldolor®) at the indicated dosages.

To be eligible for this study, the patients in the study met all of the following criteria: be hospitalized; have new (not chronic, within last 7 days) onset of fever, documented by temperature greater than or equal to 101.0° F. (38.3° C.) (the preferred method of temperature measurement was core. If a non-core route was used, temperature measurement should have been verified by an additional route of measurement; the route of temperature measurement used immediately before randomization was used immediately before dosing and for all temperature measurements during the treatment period); had adequate intravenous access; and understood and abided by the study requirements. Randomization was stratified on the basis of the severity of the patient's condition (critically ill or non-critically ill), at the time of randomization. At least 33% of the subjects randomized were to be critically ill (in the hospital requiring mechanical ventilation for respiratory failure, pressor support for hypotension, or both), and at least 33% were to not be critically ill.

The test product, dose and mode of administration was intravenous ibuprofen: 100, 200 or 400 mg, intravenous; the reference product, dose and mode of administration was normal saline, 100 ml, intravenous. The duration of treatment was 6 doses, one dose every 4 hours. Plasma ibuprofen levels were obtained for pharmacokinetic analyses at baseline and hours 0.5, 1, 1.5, 2, 2.5, 3, 3.5, 4, 6, 8, 10, 12, 14, 16, 18, 20, 22 and 24 from a subset of subjects (n=98).

Analysis of the data sets assessing the efficacy of intravenous ibuprofen (IVIb) for the treatment of fever in non-critically ill and critically ill hospitalized patients revealed a difference in pharmacokinetics and treatment effect on reduction in temperature. The Cmax and AUC for all doses of IVIb were significantly reduced in critically ill patients when compared to non-critically ill patients, while the pharmacokinetics remained first order in both patient populations. Table 1 presents the summary pharmacokinetic parameters determined from the patients enrolled in the study, by IVIb dose level and stratum.

TABLE 1

Summary of Pharmacokinetic Parameters by IVIb Dose Level and Stratum

| Treatment, Stratum | | | $AUC_{0-4}$ (ug · h/mL) | $Cmax_{0-4}$ (ug/mL) | $Tmax_{0-4}$ (h) | $Cmin_{dose1}$ (ug/mL) | $Tmin_{dose1}$ (h) | $Cmin_{dose6}$ (ug/mL) | $Tmin_{dose6}$ (h) | Thalf (h) | $AUC_{0-4}$/Dose |
|---|---|---|---|---|---|---|---|---|---|---|---|
| 100 mg IVIb | Critically Ill | N | 9 | 9 | 9 | 9 | 9 | 6 | 6 | 6 | 9 |
| | | Mean | 16.101 | 8.230 | 0.6 | 2.193 | 4.0 | 2.3 | 25.7 | 2.42 | 161.01 |
| | | Stdev | 14.638 | 6.348 | 0.2 | 2.688 | 0.0 | 1.8 | 0.8 | 1.49 | 146.38 |
| | | Min | 3.760 | 3.679 | 0.5 | 0.000 | 4.0 | 0.4 | 24.0 | 0.19 | 37.60 |
| | | Max | 50.307 | 23.839 | 1.0 | 8.180 | 4.0 | 4.7 | 26.0 | 4.79 | 503.07 |
| | Non-critically Ill | N | 14 | 15 | 15 | 14 | 14 | 14 | 14 | 14 | 14 |
| | | Mean | 26.328 | 14.530 | 0.5 | 2.945 | 4.0 | 2.6 | 26.0 | 2.49 | 263.28 |
| | | Stdev | 9.954 | 6.043 | 0.1 | 1.166 | 0.0 | 1.4 | 0.0 | 1.04 | 99.54 |
| | | Min | 7.197 | 5.234 | 0.5 | 0.508 | 4.0 | 0.3 | 26.0 | 1.31 | 71.97 |
| | | Max | 42.139 | 24.667 | 1.0 | 4.416 | 4.0 | 5.7 | 26.0 | 4.90 | 421.39 |

TABLE 1-continued

Summary of Pharmacokinetic Parameters by IVIb Dose Level and Stratum

| Treatment, Stratum | | | $AUC_{0-4}$ (ug·h/mL) | $Cmax_{0-4}$ (ug/mL) | $Tmax_{0-4}$ (h) | $Cmin_{dose1}$ (ug/mL) | $Tmin_{dose1}$ (h) | $Cmin_{dose6}$ (ug/mL) | $Tmin_{dose6}$ (h) | Thalf (h) | $AUC_{0-4}$/Dose |
|---|---|---|---|---|---|---|---|---|---|---|---|
| 200 mg IVIb | Critically Ill | N | 9 | 9 | 9 | 9 | 9 | 9 | 9 | 9 | 9 |
| | | Mean | 19.615 | 11.455 | 0.5 | 2.293 | 3.8 | 1.9 | 26.0 | 2.56 | 98.07 |
| | | Stdev | 7.014 | 2.760 | 0.0 | 1.697 | 0.4 | 2.1 | 0.0 | 1.57 | 35.07 |
| | | Min | 9.806 | 7.885 | 0.5 | 0.556 | 3.0 | 0.3 | 26.0 | 1.26 | 49.03 |
| | | Max | 30.987 | 16.390 | 0.5 | 5.393 | 4.0 | 6.4 | 26.0 | 5.11 | 154.93 |
| | Non-critically Ill | N | 17 | 17 | 17 | 17 | 17 | 17 | 17 | 16 | 17 |
| | | Mean | 39.510 | 22.893 | 0.5 | 4.732 | 3.9 | 3.0 | 26.0 | 1.86 | 197.55 |
| | | Stdev | 17.383 | 10.968 | 0.1 | 2.743 | 0.2 | 3.2 | 0.0 | 0.53 | 86.92 |
| | | Min | 9.367 | 7.788 | 0.5 | 0.542 | 3.0 | 0.3 | 26.0 | 1.23 | 46.83 |
| | | Max | 70.212 | 49.913 | 1.0 | 10.895 | 4.0 | 13.7 | 26.0 | 3.36 | 351.06 |
| 400 mg IVIb | Critically Ill | N | 10 | 10 | 10 | 10 | 10 | 9 | 9 | 9 | 10 |
| | | Mean | 45.937 | 25.701 | 0.5 | 4.689 | 3.9 | 5.0 | 26.0 | 2.32 | 114.84 |
| | | Stdev | 16.195 | 8.313 | 0.0 | 2.936 | 0.3 | 4.3 | 0.0 | 0.84 | 40.49 |
| | | Min | 25.753 | 16.664 | 0.5 | 0.850 | 3.0 | 2.0 | 26.0 | 1.53 | 64.38 |
| | | Max | 80.147 | 42.542 | 0.5 | 10.453 | 4.0 | 12.7 | 26.0 | 4.01 | 200.37 |
| | Non-critically Ill | N | 15 | 15 | 15 | 15 | 15 | 14 | 14 | 14 | 15 |
| | | Mean | 87.113 | 49.128 | 0.5 | 10.657 | 3.8 | 6.6 | 26.0 | 2.22 | 217.78 |
| | | Stdev | 29.188 | 16.141 | 0.0 | 4.822 | 0.4 | 5.4 | 0.0 | 1.05 | 72.97 |
| | | Min | 37.351 | 20.310 | 0.5 | 3.677 | 3.0 | 1.7 | 26.0 | 1.48 | 93.38 |
| | | Max | 141.771 | 72.257 | 0.5 | 22.294 | 4.0 | 23.8 | 26.0 | 5.54 | 354.43 |

Figure 2:
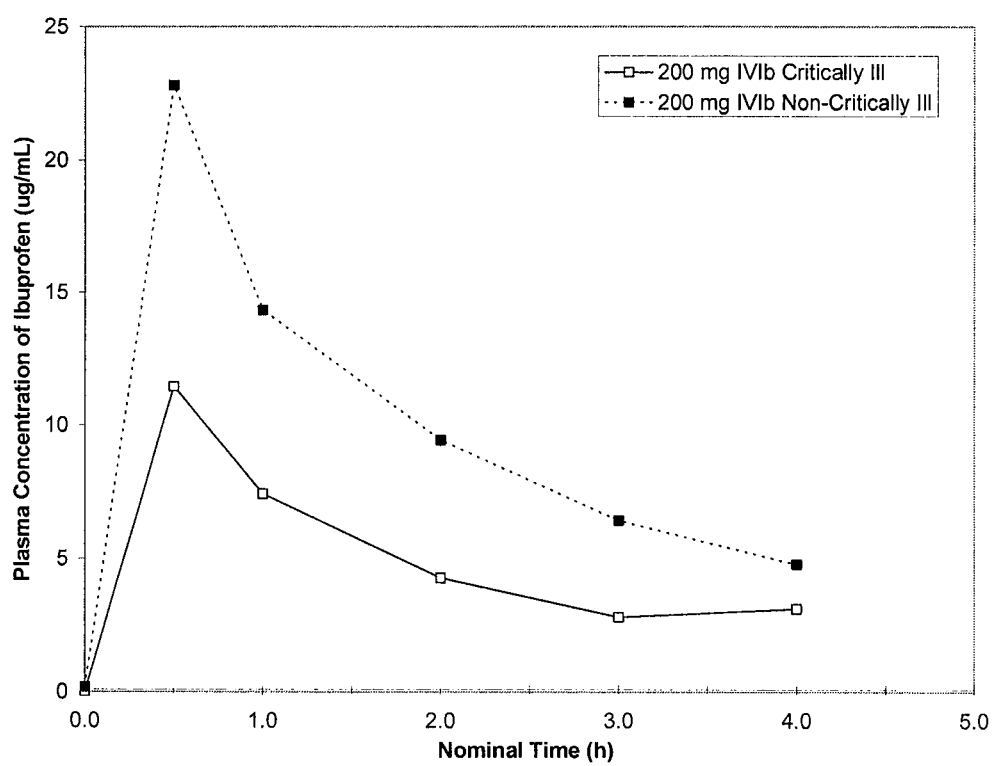
FIG. 2 shows mean ibuprofen plasma concentrations (hours 0-4), following administration of 200 mg IVIb in critically ill versus non-critically ill patients.
Figure 3:
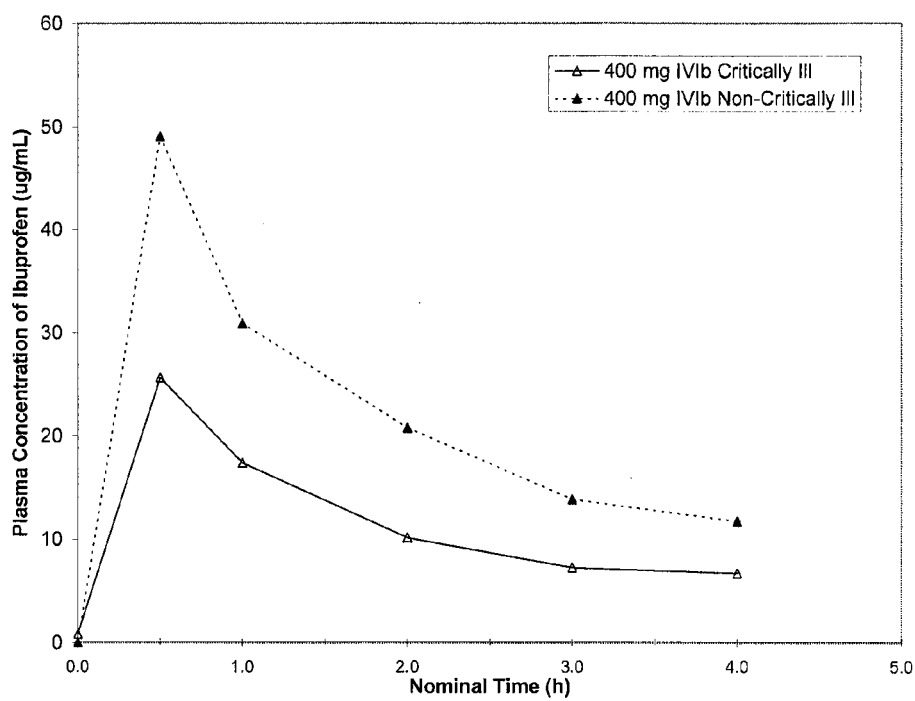
FIG. 3 shows mean ibuprofen plasma concentrations (hours 0-4) following administration of 400 mg IVIb in critically ill versus non-critically ill patients.

FIGS. 1, 2 and 3 present the Cmax graphically for the treatment groups, by stratum.

Figure 4:
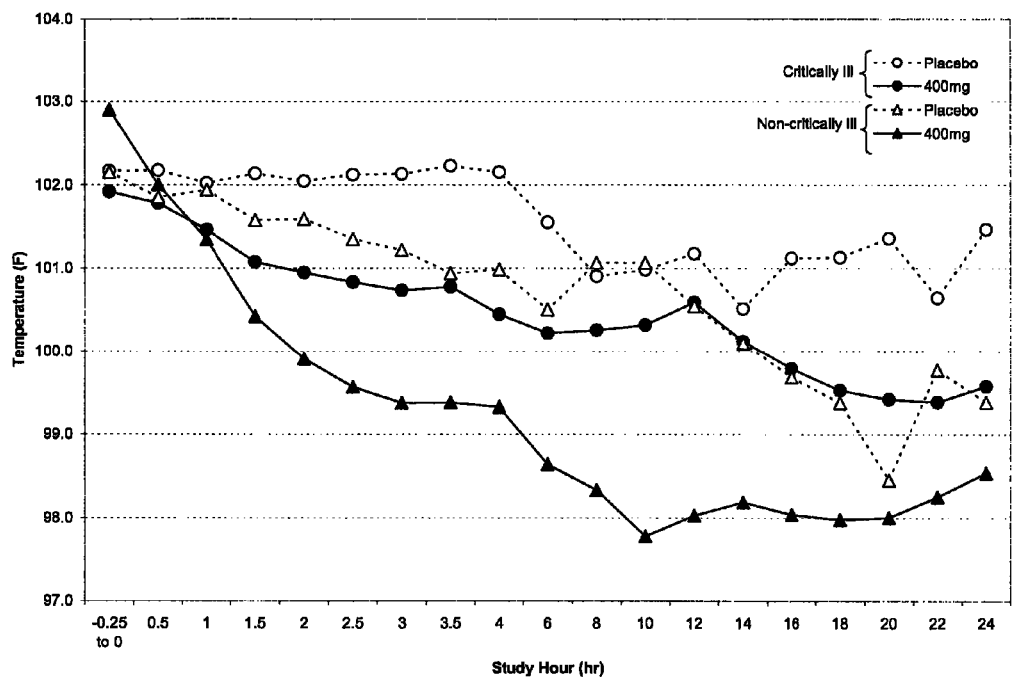
FIG. 4 shows temperature over time by stratum, 400 mg IVIb vs. placebo.

The efficacy of IVIb for the treatment of fever in the non-critically and critically ill patients was examined to better understand the clinical relevance of the pharmacokinetic difference presented in the study. FIG. 4 compares the effect of placebo and a 400 mg dose of IVIb on body temperature in non-critically and critically ill hospitalized patients. These data suggest that severity of illness appears to lower Cmax and AUC of IVIb which appears to limit the therapeutic effect.

At 4 hours, in the "intention to treat" (ITT) population, 24 of 31 (77%) of subjects in the 400 mg IVIb group, compared to 9 of 28 (32%) of the placebo group had a temperature less than 101.0° F. (or 38.3° C.), p=0.0005, also clearly demonstrating the efficacy of the 400 mg dose of IVIb on reducing fever and meeting the primary endpoint.

Further, doses of 100 mg and 200 mg were also found to be statistically significant in reducing fever at the 4 hour primary endpoint.

There were no statistically significant differences between treatment groups compared with placebo in terms of adverse event occurrence (limited to events occurring in at least 3 subjects) except for bacteremia where the incidence was 13% in the 100 mg treatment group (n=4) vs. 0% in the placebo group (p=0.045). There were no statistically significant differences in the occurrence of serious adverse events or deaths in any treatment group when compared with placebo.

While 400 mg is proposed as the effective dose for the indication of reduction of fever, a dose adjustment up to 800 mg for the treatment of fever may be warranted if the reduction in fever at a lower dose is not adequate. Table 2 presents the percent (%) difference between the critically ill versus the non-critically ill stratums for the $AUC_{0-4}$ and $Cmax_{0-4}$ pharmacokinetic parameters.

TABLE 2

Pharmacokinetic Parameters Differences in the 400 mg IVIb Dose Level and Stratum

| Treatment, Stratum | | $AUC_{0-4}$ (ug·h/mL) | $Cmax_{0-4}$ (ug/mL) |
|---|---|---|---|
| 100 mg IVIb | Critically Ill | 16.10 | 8.23 |
| | Non-critically Ill | 26.33 | 14.53 |
| | Critically Ill/Non-critically Ill % Difference | 61.2% | 56.6% |
| 200 mg IVIb | Critically Ill | 19.62 | 11.46 |
| | Non-critically Ill | 39.51 | 22.89 |
| | Critically Ill/Non-critically Ill % Difference | 49.6% | 50.0% |
| 400 mg IVIb | Critically Ill | 45.94 | 25.70 |
| | Non-critically Ill | 87.11 | 49.13 |
| | Critically Ill/Non-critically Ill % Difference | 52.7% | 52.3% |

The values for the AUC and Cmax pharmacokinetic parameters for the critically ill patients were approximately 50% compared to the parameters for the non-critically ill patients. This difference suggests that the dose may need to be increased from 400 mg up to 800 mg for treatment of fever, depending upon the severity of illness for the patient being treated.

Based on the overall efficacy and safety results, IVIB appears to be both safe and effective in reducing fever in both critically ill and non-critically ill patients.

Example 2

This study was a randomized, double-blind, placebo-controlled, single dose, crossover study of the pharmacokinetics, safety and tolerability of ibuprofen injection (IVIb) in healthy adult volunteers. It evaluated the pharmacokinetics profile of a single dose of IVIb administered over 5-7 minutes.

Twelve subjects were randomized in equal proportion to one of two sequences:

Sequence A: A single dose of IVIb and oral placebo administered concurrently on Day 1 of the Treatment Period followed by a single dose of oral ibuprofen and intravenous placebo given concurrently on Day 8 of the Treatment Period. Days 2-7 were a washout period.

Sequence B: A single dose of oral ibuprofen and intravenous placebo administered concurrently on Day 1 of the Treatment Period followed by a single dose of IVIb and oral placebo given concurrently on Day 8 of the Treatment Period. Days 2-7 were a washout period.

In each Period, subjects received a single dose of ibuprofen 800 mg, as one of:
  8 mL IVIb 100 mg/ml added to 192 mL of normal saline, along with placebo capsule;
  800 mg tablet ibuprofen, along with 200 mL of normal saline IV.

The oral dose was administered with approximately 240 ml of water.

Pharmacokinetics parameters in plasma were determined for all 12 subjects. Averages (and standard deviations) by treatment of key plasma pharmacokinetics parameters of ibuprofen (IVIb and oral) are provided in Table 3 below:

TABLE 3

| Treatment | $C_{max}$ (μg/mL) | $AUC_{0\text{-}tlast}$ (h * μg/mL) | $AUC_{0\text{-}12}$ (h * μg/mL) | $AUC_{0\text{-}inf}$ (h * μg/mL) | $t_{1/2}$ (h) |
|---|---|---|---|---|---|
| IVIb | 120 | 188 | 191 | 196 | 2.0 |
|  | (13) | (37) | (36) | (37) | (0.5) |
| Oral Ibuprofen | 63 | 189 | 191 | 196 | 1.9 |
|  | (12) | (36) | (36) | (36) | (0.3) |

Median $T_{max}$ was 0.11 hours (6.5 minutes) for IVIb and 1.50 hours for oral ibuprofen.

The comparison between treatments showed that intravenous ibuprofen (IVIb) had equivalent bioavailability to oral ibuprofen, as determined by the mean ratio of geometric least squares means of AUC0-tlast (mean ratio 100%, with 90% confidence interval 90%-112%). The mean Cmax of IVIb was approximately twice that of the oral dose. The median Tmax of the oral dose was 1.50 hours compared with 6.5 minutes for the intravenous infusion over 5-7 minutes. In this study, intravenous ibuprofen (IVIb) was found to be safe and well tolerated when administered over a period of five to seven minutes.

Example 3

In a prior study, in which pharmacokinetic samples were not obtained, IVib (Caldolor®) dosing was up to 800 mg IVIb every six hours. That dosage regimen resulted in a significant and sustained reduction in fever throughout the 48 hour dosing period. Since the majority of the patients in that trial would be considered as critically ill given the definition in the study reported in this Example, the results of that prior study support a dose up to 800 mg if required.

More particularly, this was a randomized, double blind, placebo-controlled study of intravenous ibuprofen in participants with severe sepsis. Participants meeting criteria for severe sepsis syndrome were enrolled and randomized to receive either intravenous ibuprofen or glycine buffer vehicle diluted and administered in Normal Saline, Lactated Ringers, or D5W (dextrose 5% in water). Participants received either Ibuprofen Injection 50 mg/mL or the placebo vehicle consisting of a glycine buffer, both of which were administered intravenously over 30-60 minutes every 6 hours for 8 doses. Participants were followed for a total of 30 days or until hospital discharge or death.

Figure 5:
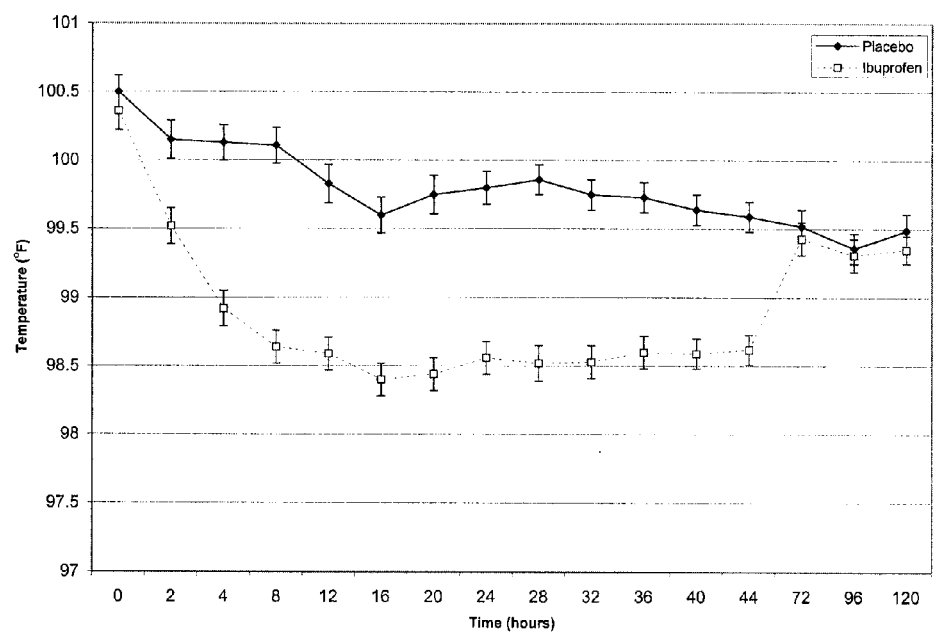
FIG. 5 shows the difference in mean temperature in critically ill patients in Example 3 for IVIb versus placebo.

For all enrolled patients at baseline, the mean temperature was 100.5±0.12 for the placebo group and 100.4±0.14 for the ibuprofen treated group. Within two hours after dosing with IVib, the ibuprofen treated group had a statistically significant lower temperature than the placebo treated group (100.2±0.14 Placebo, 99.5±0.13 Ibuprofen, p=0.001). The difference remained significant through the 44 hour assessment; 2 hours after administration of the final dose of IVib (FIG. 5). After the IVib was discontinued, no statistically significant differences were noted between the placebo and ibuprofen groups.

It was concluded that ibuprofen delivered intravenously at a dose of 10 mg/kg (maximum 800 mg) every 6 hours for 8 doses to subjects with severe sepsis does not alter 14-day or 30-day all-cause mortality nor does it alter the rate of organ failure or organ failure reversal. Ibuprofen does reduce the fever, tachycardia, tachypnea and lactic acidosis associated with severe sepsis. Short term use of relatively high doses of intravenous ibuprofen does not produce clinically significant side effects or toxicity.

Based on the data obtained in this study, along with the pharmacokinetic data obtained from the study reported in Example 2, it is surmised that the Cmax and AUC levels obtained for the 800 IVib dose in critically ill patients is about one/half (50%) of the Cmax and AUC obtained for non-critically ill patients. It is further estimated that the 800 mg IVib dose will attain a mean Cmax within 80-125% of about 60 μg/ml and an $(AUC)_{0\text{-}t}$ within 80-125% of about 94 μg·h/ml in critically ill patients. The Cmax figure is obtained by calculating one half of the Cmax for the 800 mg IVib dose in non-critically ill patients (120 μg/ml). The AUC is likewise obtained by calculating one half of the $(AUC)_{0\text{-}t}$ obtained for non-critically ill patients (188 μg·h/ml).

CONCLUSION

It will be readily apparent to one of ordinary skill in the relevant arts that other suitable modifications and adaptations to the methods and applications described herein are suitable and may be made without departing from the scope of the invention or any embodiment thereof. While the invention has been described in connection with certain embodiments, it is not intended to limit the invention to the particular forms set forth, but on the contrary, it is intended to cover such alternatives, modifications and equivalents as may be included within the spirit and scope of the invention as defined by the following claims.

We claim:

1. A method of treating pain in critically ill patients in need thereof, comprising administering to critically ill patients an intravenous ibuprofen pharmaceutical composition in a dose of about 800 mg and providing a mean Cmax of about 60 μg/ml to treat pain in said patients, wherein the critically ill patients are not suffering from inflammation and are receiving at least one treatment selected from vasopressor support and mechanical ventilation.

2. The method of claim 1 wherein the pharmaceutical composition is an aqueous solution of arginine and ibuprofen.

3. The method of claim 1, wherein the molar ratio of arginine to ibuprofen is selected from less than or equal to 1:1, less than or equal to 0.99:1, less than or equal to 0.98:1, less than or equal to 0.97:1, less than or equal to 0.96:1, less than or equal to 0.95:1, less than or equal to 0.94:1, less than or equal to 0.93:1, less than or equal to 0.92:1, less than or equal to 0.91:1, less than or equal to 0.90:1, less than or equal to 0.60:1.

4. A method of treating pain in critically ill patients in need thereof, comprising administering to critically ill patients who are in pain, not suffering from inflammation and are selected from the group consisting of patients who are being administered large volumes of blood products; are receiving multiple antibiotics; have a pulmonary artery catheter or an arterial blood pressure catheter inserted; and combinations of any of the foregoing, an intravenous ibuprofen pharmaceutical composition in a dose of 800 mg such that the dose reduces pain in the critically ill patients.

5. The method of claim 4, wherein the dose of intravenous ibuprofen administered to the critically ill patients provides a mean Cmax of about 60 μg/ml.

6. The method of claim 5, wherein the dose of intravenous ibuprofen administered provides a mean $(AUC)0\text{-}t$ within about 80% to about 125% of 94 μg.h/ml.

7. The method of claim 4, further comprising selecting a dosage interval for the critically ill patients from dosing intervals of greater than 4 hours and greater than 6 hours.

8. The method of claim 4, further comprising administering the pharmaceutical composition as an aqueous solution of arginine and ibuprofen.

9. The method of claim 8, wherein the molar ratio of arginine to ibuprofen is selected from less than or equal to 1:1, less than or equal to 0.99:1, less than or equal to 0.98:1, less than or equal to 0.97:1, less than or equal to 0.96:1, less than or equal to 0.95:1, less than or equal to 0.94:1, less than or equal to 0.93:1, less than or equal to 0.92:1, less than or equal to 0.91:1, less than or equal to 0.90:1, less than or equal to 0.60:1.

10. The method of claim 1, wherein the critically ill patients are patients who: are being treated in an Intensive Care Unit; are being administered large volumes of blood products; are undergoing dialysis; are receiving multiple antibiotics; have a pulmonary artery catheter or an arterial blood pressure catheter inserted; and combinations of any of the foregoing.

11. The method of claim 1, further comprising selecting a dosage interval for the critically ill patients of every 4 to 6 hours.

12. The method of claim 4, further comprising selecting a dosage interval for the critically ill patients of every 4 to 6 hours.

13. The method of claim 1, further comprising selecting a dosage interval for the critically ill patients from dosing intervals of greater than 4 hours and greater than 6 hours.

* * * * *